United States Patent [19]

Ogino et al.

[11] Patent Number: 4,803,010

[45] Date of Patent: Feb. 7, 1989

[54] WATER-SOLUBLE VISCOSITY INCREASING AGENT AND DETERGENT COMPOSITION CONTAINING THE SAME

[75] Inventors: Hidekazu Ogino, Koutoubashi; Hiroshi Kamitani, Wakayama; Jun Kamegai, Ichikawa; Hiroki Sawada, Wakayama; Hajime Hirota, Tokyo; Tomihiro Kurosaki, Sennan, all of Japan

[73] Assignee: Kao Corporation, Tokyo, Japan

[21] Appl. No.: 93,606

[22] Filed: Sep. 8, 1987

[30] Foreign Application Priority Data

Sep. 18, 1986 [JP] Japan .............................. 61-220043
Sep. 18, 1986 [JP] Japan .............................. 61-220044

[51] Int. Cl.$^4$ .............................................. C11D 1/72
[52] U.S. Cl. ................................ 252/174.21; 252/108; 252/173; 252/174.16; 252/174.22; 252/544; 252/545; 252/546; 252/547; 252/553; 252/559; 252/DIG. 5; 252/DIG. 13; 252/DIG. 14; 260/410.6; 560/263
[58] Field of Search ............... 252/174.21, 174.22, 252/DIG. 14, DIG. 13, DIG. 5, 89.1, 173, DIG. 1; 260/410.6; 560/263

[56] References Cited

U.S. PATENT DOCUMENTS

| | | | |
|---|---|---|---|
| 2,269,529 | 1/1942 | Goldsmith | 260/410.6 |
| 2,366,737 | 1/1945 | Loder et al. | 260/410.6 |
| 2,904,585 | 9/1959 | Doerr et al. | 260/410.6 |
| 4,097,403 | 6/1978 | Tsutsumi et al. | 260/410.6 |

FOREIGN PATENT DOCUMENTS

2129004  5/1984  United Kingdom .

*Primary Examiner*—Paul Lieberman
*Assistant Examiner*—Hoa Van Le
*Attorney, Agent, or Firm*—Oblon, Fisher, Spivak, McClelland & Maier

[57] ABSTRACT

A water-soluble viscosity increasing agent consisting essentially of: (i) an ester of a 40 to 400 moles ethylene oxide adduct of polyhydric alcohol and a $C_{8-36}$ branched fatty acid, (ii) an ester of polyethylene glycol having average molecular weight of 2,000 to 20,000 and a $C_{8-36}$ branched fatty acid, and (iii) a 40 to 400 mole ethylene oxide adduct of an ester of a polyhydric alcohol and a $C_{8-36}$ branched fatty acid. The viscosity increasing agent can increase the viscosity of solutions of various surface active agents, while maintaining their stability and solubility in the solutions. When it is formulated to a detergent suitable for washing textiles, tablewares, human skins, hairs and the like, it can provide a detergent composition with a proper viscosity as well as a good detergency.

9 Claims, No Drawings

WATER-SOLUBLE VISCOSITY INCREASING AGENT AND DETERGENT COMPOSITION CONTAINING THE SAME

BACKGROUND OF THE INVENTION

1. Field of the Invention

This invention relates to a water-soluble viscosity increasing agent and a liquid detergent composition containing the same and, more particularly, to a water-soluble viscosity increasing agent having excellent stability and solubility in a solution of various surface active agents and to a liquid detergent composition possessing a proper viscosity and homogeneousness containing said water-soluble viscosity increasing agent.

2. Description of the Background

Viscosity increasing agents are used in order to impart an appropriate viscosity to solutions of various surface active agents such as, for example, anionic, cationic and nonionic surface active agents, and have a wide variety of applications, e.g., for liquid detergents, cosmetics, paints, adhesives, dyestuff and the like. As viscosity increasing agents to be used with said solutions of a surface active agent, polyoxyethylene (hereinafter abbreviated to "POE") linear fatty acid ester type compounds, including POE linear fatty acid esters and POE methylglucoside linear fatty acid esters, and water-soluble polymers such as hydroxyethyl cellulose, methyl cellulose, polyvinyl pyrrolidone and the like are known in the art.

The viscosity increasing agents of the POE linear fatty acid ester type, however, tend to hydrolyze in an aqueous system and have a poor viscosity stability. On the other hand, the viscosity increasing agents of the water-soluble polymer type tend to salt out in a strong electrolyte solution containing a certain kind of an anionic surface active agent or inorganic salt, and thus have a poor solubility to such electrolyte. This imposes a serious limitation to the formulation, for example, of shampoos, when one intends to increase their viscosity.

There have been, therefore, strong demands for the development of a viscosity increasing agent possessing a good viscosity stability and an abundant solubility to solutions of various surface active agents, including anionic, cationic and nonionic surface active agents.

SUMMARY OF THE INVENTION

In these situations, the present inventors have made extensive studies, and found that ethylene oxide adducts of a polyhydric alcohol, esters of branched fatty acid and ethylene glycol and ethylene oxide adducts of branched fatty acid esters of polyhydric alcohol are capable of enhancing viscosity of solutions of surface active agents, while maintaining stability of the solutions and giving a good solubility of surface active agents in the solutions. The effects are such that one can never anticipate with conventional linear fatty acid esters. Such findings have led to the completion of this invention.

Accordingly, an object of this invention is to provide a water-soluble viscosity increasing agent consisting essentially of one or more branched fatty acid esters selected from the group consisting of the following (i) to (iii):

(i) an ester of a 40 to 400 moles ethylene oxide adduct of polyhydric alcohol and a branched fatty acid of 8 to 36 carbon atom content, (ii) an ester of polyethylene glycol having average molecular weight of 2,000 to 20,000 and branched fatty acid of 8 to 36 carbon atom content, and (iii) a 40 to 400 mole ethylene oxide adduct of an ester of a polyhydric alcohol and a branched fatty acid of 8 to 36 carbon atom content.

The second object of this invention is to provide a liquid detergent composition comprising 5 to 40% by weight of a surface active agent having a detergency and 0.1 to 10% by weight of the above water-soluble viscosity increasing agent.

DETAILED DESCRIPTION OF THE INVENTION AND PREFERRED EMBODIMENTS

The ethylene oxide adducts of a polyhydric alcohol, esters of a branched fatty acid and ethylene glycol, and ethylene oxide adducts of branched fatty acid ester of polyhydric alcohol to be employed in this invention may be prepared according to the methods known in the art, with no special limitation being imposed to the processes and their conditions. Examples of these methods include a method of reacting a polyhydric alcohol with a branched fatty acid in the presence of an alkali catalyst or an acid catalyst to afford a polyhydric alcohol branched fatty acid ester and then adding ethylene oxide to the polyhydric alcohol branched fatty acid ester in the presence of an alkali catalyst, a method of adding ethylene oxide to a polyhydric alcohol in the presence of an alkali catalyst and then esterifying the thus-obtained ethylene oxide adduct with a branched fatty acid, a method of reacting polyethylene glycol with a branched fatty acid in the presence of an alkali catalyst or an acid catalyst, and a method of effecting an addition reaction of a branched fatty acid and ethylene oxide (for preparing a branched fatty acid ester of polyethylene glycol).

The branched fatty acids to be used in the above methods are preferably a branched fatty acid having from 8 to 36 carbon atoms. More preferably the branched fatty acid is an α-position branched fatty acid represented by the following formula (I):

in which $R_1$ represents a linear or branched alkyl or alkenyl group of 4 to 18 carbon atom content and $R_2$ represents a linear or branched alkyl or alkenyl group of 2 to 16 carbon atom content.

These are specifically 2-ethylhexanoic acid, 2-ethyl-iso-hexanoic acid, 2-propylheptanoic acid, 2-propyl-iso-heptanoic acid, 2-butyloctanoic acid, 2-iso-butyloctanoic acid, 2-pentylnonanoic acid, 2-iso-pentylnonanoic acid, 2-hexyldecanoic acid, 2-hexyl-iso-decanoic acid, 2-butyldodecanoic acid, 2-iso-butyldodecanoic acid, 2-heptylundecanoic acid, 2-iso-heptylundecanoic acid, 2-iso-heptyl-iso-undecanoic acid, 2-dodecylhexanoic acid, 2-iso-dodecylhexanoic acid, 2-octyldodecanoic acid, 2-iso-octyldodecanoic acid, 2-octyl-iso-dodecanoic acid, 2-nonyltridecanoic acid, 2-iso-nonyl-iso-tridecanoic acid, 2-decyldodecanoic acid, 2-iso-decyldodecanoic acid, 2-decyl-iso-dodecanoic acid, 2-decyltetradecanoic acid, 2-octylhexadecanoic acid, 2-iso-octylhexadecanoic acid, 2-undecylpentadecanoic acid, 2-iso-undecylpentadecanoic acid, 2-dodecylheptadecanoic acid, 2-iso-dodecyl-iso-heptadecanoic acid, 2-decyloctadecanoic acid, 2-decyl-iso-octadecanoic acid, 2-tridecylheptadecanoic acid, 2-iso-tridecyl-iso-heptadecanoic acid, 2-tetradecyloctadecanoic acid, 2-iso-tetradecyloctadecanoic acid, 2-hexadecylhexadecanoic acid, 2-hexadecyltetradecanoic acid, 2-hexadecyl-iso-hexadecanoic acid, 2-iso-hexadecyl-iso-hexadecanoic acid, 2-pentadecylnonadecanoic acid, 2-iso-pentadecyl-iso-nonadecanoic acid, 2-tetradecylbehenic acid, 2-iso-tetradecylbehenic acid, 2-iso-tetradecylbehenic acid, 2-tetradecyl-iso-behenic acid, 2-iso-tetradecyl-iso-behenic acid, and the like.

As a polyhydric alcohol, alcohols of more than trivalent are desirably used. Examples of these polyhydric alcohols are glycerol, trimethylolpropane, pentaerythritol, arabinitol, xylitol, sorbitol, mannitol, galactitol, heptytol, inositol, sorbitan, sorbide, glucose, galactose, mannose, maltose, fructose, sucrose, lactose, maltitol, lactitol, methylglucoside, methylgalactoside, methylmannoside, methylmaltoside, and the like. Among these, preferred polyhydric alcohols are glycerol, trimethylolpropane, pentaerythritol, sorbitol, mannitol, sorbitan, sorbide, inositol and methylglucoside in view of the thermal stability, economy and viscosity increasing effects.

Moles of ethylene oxide to be added may be 40 to 400, preferably 80 to 300, per 1 mole of the raw material, i.e. the polyhydric alcohol branched fatty acid ester or polyhydric alcohol.

Polyethylene glycol to be used may be that having a molecular weight of 2,000 to 20,000, preferably 3,500 to 15,000.

The branched fatty acid is used from 1 to 8 moles per 1 mole of the raw material, i.e. the polyoxyethylene polyhydric alcohol ether or polyhydric alcohol.

The esterification degree of the branched fatty acid ester to be employed in this invention may be 1 to 8, preferably 1.0 to 5.0. The branched fatty acid esters may be used either singly or mixed with one or more others at an arbitrary ratio.

In case where the branched fatty acid esters are used as the component (B) of the liquid detergent composition of the second invention, the amount of these compounds to be formulated may be 0.1 to 10% by weight, preferably 0.4 to 4% by weight per total amount of the liquid detergent composition.

Following compounds are given as examples of surface active agents having a detergency to be employed for the component (A) of the second invention:

(1) Linear or branched alkylbenzenesulfonates having an alkyl group with an average carbon atom content of 10 to 16.

(2) Alkyl- or alkenylether sulfates added with 0.5 to 8 moles, per molecule in average, of ethylene oxide, propylene oxide, butylene oxide, ethylene oxide/propylene oxide at a ratio of 0.1/9.9 to 9.9/0.1 and ethylene oxide/butylene oxide at a ratio of 0.1/9.9 to 9.9/0.1, and having an alkyl- or alkenyl group with an average carbon atom content of 10 to 20.

(3) Alkyl- or alkenyl sulfates having an alkyl- or alkenyl group with an average carbon atom content of 10 to 20.

(4) Olefin sulfonates having an average carbon atom content of 10 to 20 per molecule.

(5) Alkane sulfonates having an average carbon atom content of 10 to 20 per molecule.

(6) Salts of a saturated or unsaturated fatty acid having an average carbon atom content of 10 to 24 per molecule.

(7) Alkyl- or alkenylether carboxylates added with, per molecule, 0.5 to 8 moles in average of ethylene oxide, propylene oxide, butylene oxide, ethylene oxide/propylene oxide at a ratio of 0.1/9.9 to 9.9/0.1 and ethylene oxide/butylene oxide at a ratio of 0.1/9.9 to 9.9/0.1, and having an alkyl- or alkenyl group with an average carbon atom content of 10 to 20.

(8) Salts of α-sulfofatty acid represented by the following formula:

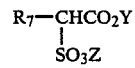

in which Y represents an alkyl group of from 1 to 3 carbon atom content or a counter ion, Z represents a counter ion and $R_7$ represents an alkyl or alkenyl group of from 10 to 20 carbon atom content; or esters thereof.

A counter ion of an anionic surface active agent to be used in the present invention may include alkali metal ions such as sodium and potassium ions, alkaline earth metal ions such as calcium and magnesium ions, ammonium ion, alkanol amines having from 1 to 3 alkanol groups of a 2 or 3 carbon atom content such as monoethanol amine, diethanol amine, triethanol amine and isopropanol amine, and the like.

(9) Amino acid type surface active agents represented by the following formulae:

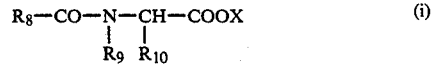

in which $R_8$ represents an alkyl- or alkenyl group of from 8 to 24 carbon atom content, $R_9$ represents hydrogen atom or an alkyl group of 1 or 2 carbon atom content, $R_{10}$ represents an amino acid group residue and X represents an alkali or alkaline earth metal ion.

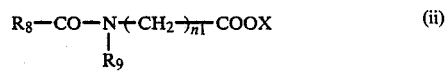

in which $R_8$, $R_9$ and X have the same meanings as defined above, and n1 represents an integer of 1 to 5.

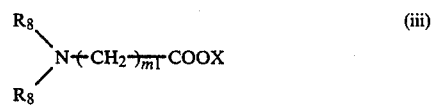

in which $R_8$ and X have the same meanings as defined above, and m1 represents an integer of 1 to 8.

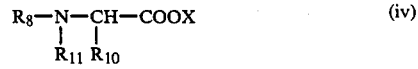

in which $R_8$, $R_{10}$ and X have the same meanings as defined above and $R_{11}$ represents hydrogen atom or an alkyl or hydroxyalkyl group of 1 or 2 carbon atom content.

$$R_{12}-\underset{\underset{R_9}{|}}{N}-\underset{\underset{R_{10}}{|}}{CH}-COOX \qquad (v)$$

in which $R_9$, $R_{10}$ and X have the same meanings as defined above and $R_{12}$ represents a β-hydroxyalkyl or β-hydroxyalkenyl group of from 6 to 28 carbon atom content.

$$\underset{R_{12}}{\overset{R_{12}}{\diagdown}}N-\underset{\underset{R_{10}}{|}}{CH}-COOX \qquad (iii)$$

in which $R_{10}$, $R_{12}$ and X have the same meanings as defined above.

(10) Phosphoric acid ester type surface active agents (i) Acidic alkyl- or alkenyl phosphoric acid esters represented by the following formula:

$$(R_8O)_{n2}-\overset{\overset{O}{\|}}{P}(OH)_{m2}$$

in which $R_8$ has the same meaning as defined above, and n2 and m2 are values satisfying the equation, n2+m2=3, provided that n2 is a value of 1 to 2.

(ii) Alkyl- or alkenyl phosphoric acid esters represented by the following formula:

$$R_8O-\underset{\underset{O}{\|}}{\overset{\overset{OR_8}{|}}{P}}-OR_8$$

in which $R_8$ has the same meaning as defined above.

(iii) Salts of an alkyl- or alkenyl phosphoric acid ester represented by the following formula:

$$(R_8O)_{n3}-\overset{\overset{O}{\|}}{P}(OM)_{m3}$$

in which $R_8$ has the same meaning as defined above, M denotes sodium, potassium or calcium, and n3 and m3 are values satisfying the equation n3+m3=3, provided that n3 is a value of 1 to 3.

(11) Sulfonic acid type amphoteric surface active agents represented by the following formulae:

$$R_8CONH-R_{13}-\underset{\underset{R_{14}}{|}}{\overset{\overset{R_{14}}{|}}{N^+}}-R_{15}-SO_3^- \qquad (i)$$

in which $R_8$ has the same meaning as defined above, $R_{13}$ represents an alkylene group of 1 to 5 carbon atom content, $R_{14}$ represents an alkyl group of 1 to 4 carbon atom content, and $R_{15}$ represents an alkylene or hydroxyalkylene group of 1 to 4 carbon atom content.

$$R_8-\underset{\underset{R_{17}}{|}}{\overset{\overset{R_{16}}{|}}{N^+}}-R_{15}-SO_3^- \qquad (ii)$$

in which $R_8$ and $R_{15}$ have the same meanings as defined above, $R_{16}$ and $R_{17}$ each represents independently an alkyl group of 8 to 24 carbon atom content or an alkenyl group of 1 to 5 carbon atom content.

$$R_8-\underset{\underset{(C_2H_4O)_{n4}H}{|}}{\overset{\overset{(C_2H_4O)_{n4}H}{|}}{N^+}}-R_{15}-SO_3^- \qquad (iii)$$

in which $R_8$ and $R_{15}$ have the same meanings as defined above and n4 designates an integer of from 1 to 20.

(12) Betaine type amphoteric surface active agents represented by the following formulae:

$$R_{18}-\underset{\underset{R_{19}}{|}}{\overset{\overset{R_{19}}{|}}{N^+}}-R_{20}-COO^- \qquad (i)$$

in which $R_{18}$ represents an alkyl, alkenyl, β-hydroxyalkyl or β-hydroxyalkenyl group of from 8 to 24 carbon atom content, $R_{19}$ represents and alkyl group of from 1 to 4 carbon atom content, and $R_{20}$ represents an alkylene or hydroxyalkylene group of from 1 to 6 carbon atom content.

$$R_{18}-\underset{\underset{(C_2H_4O)_{n4}H}{|}}{\overset{\overset{(C_2H_4O)_{n4}H}{|}}{N^+}}-R_{20}-COO^- \qquad (ii)$$

in which $R_{18}$, $R_{20}$ and n4 have the same meanings as defined above.

$$R_{18}-\underset{\underset{R_{21}}{|}}{\overset{\overset{R_{21}}{|}}{N^+}}-R_{20}-COO^- \qquad (iii)$$

in which $R_{18}$, $R_{20}$ have the same meanings as defined above and $R_{21}$ represents a carboxyalkyl or hydroxyalkyl group.

(13) Polyoxyethylenealkyl- or alkenyl ethers added with from 1 to 20 moles of ethylene oxide and having an alkyl or alkylene group of an average carbon atom content of from 10 to 20.

(14) Polyoxyethylenealkylphenylethers added with from 1 to 20 moles of ethylene oxide and having an alkyl group of an average carbon atom content of from 6 to 12.

(15) Polyoxypropylenealkyl- or alkenyl ethers added with from 1 to 20 moles of propylene oxide and having an alkyl or alkenyl group of an average carbon atom content of from 10 to 20.

(16) Polyoxybutylenealkyl- or alkenyl ethers added with from 1 to 20 moles of butylene oxide and having an alkyl or alkenyl group of an average carbon atom content of from 10 to 20.

(17) Nonionic surface active agents which are total 1 to 30 moles of ethylene oxide/propylene oxide or ethylene oxide/butylene oxide addition compounds, ratio of ethylene oxide/propylene oxide or ethylene oxide/butylene oxide being 0.1/9.9 to 9.9/0.1, and which have an alkyl or alkenyl group of an average carbon atom content of from 10 to 20.

(18) Higher fatty acid alkanol amides represented by the following formula:

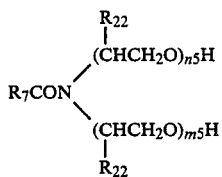

in which $R_7$ has the same meaning as defined above, $R_{22}$ represents hydrogen atom or methyl group, n5 designates an integer of from 1 to 3, and m5 designates an integer of from 0 to 3; or alkylene oxide adducts thereof.

(19) Glycerol monoesters of a fatty acid having an average carbon atom content of from 10 to 20.

(20) Alkylamine oxides represented by the following formula:

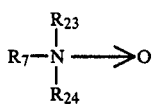

in which $R_7$ has the same meaning as defined above, $R_{23}$ and $R_{24}$ each represents independently an alkylene group of from 1 to 3 carbon atom content.

(21) Cationic surface active agents represented by the following formula:

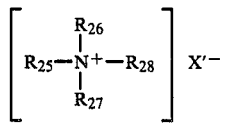

in which at least one of $R_{25}$, $R_{26}$, $R_{27}$ and $R_{28}$ is an alkyl- or alkenyl group of from 8 to 24 carbon atom content and others designate an alkyl group of from 1 to 5 carbon atom content, and $X'$ represents a halogen atom.

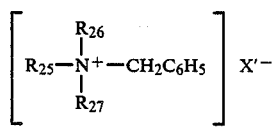

in which $R_{25}$, $R_{26}$, $R_{27}$ and $X'$ have the same meanings as defined above.

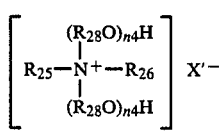

in which $R_{25}$, $R_{26}$, $X'$ and n4 have the same meanings as defined above, and $R_{28}$ represents an alkylene group of from 2 or 3 carbon atom content.

Among the surface active agents illustrated above, particularly preferred are anionic surface active agents such as linear or branched alkyl sulfates having an average carbon atom content of from 10 to 16, polyoxyethylene alkyl sulfates with 0.5 to 8 moles of POE added per molecule and the alkyl group having an average carbon atom content of from 8 to 20, alkyl phosphates having an average carbon atom content of from 8 to 16, olefin sulfonates having an average carbon atom content of from 10 to 16; nonionic surface active agents such as higher fatty acid mono- or dialkanol amide having an average carbon atom content of from 10 to 14; amphoteric surface active agents of alkylamine oxide, alkyl betaine and imidazoline type, all having an average carbon atom content of from 10 to 14. These surface active agents may be formulated either singly or in combination with others to the liquid detergent composition in an amount ranging from 5 to 40% by weight, preferably 10 to 25% by weight.

Branched fatty acid esters to be employed in this invention is insusceptible of hydrolysis due to their branched structure of the long chained alkyl group. Because of this, it is presumed that a solution containing these esters and surface active agents is not liable to the change in viscosity upon lapse of time.

The viscosity increasing agent according to the first invention of this application is capable of increasing the viscosity of solutions of various surface active agents, inclusive of anionic, nonionic and cationic surface active agents, while maintaining the stability and solubility of these surface active agents in solutions. It can be, therefore, advantageously formulated to various detergents, especially those used for washing textiles, tablewares, human skins, hairs and the like. In particular, according to the first invention in which the viscosity increasing agent is employed in combination with a surface active agent having a detergency, the composition with a proper viscosity as well as a good detergency can be obtained, which can be advantageously used as a skin detergent, a hair detergent and the like.

Other features of the invention will become apparent in the course of the following description of the exemplary embodiments which are given for illustration of the invention and are not intended to be limiting thereof.

EXAMPLES

Synthetic Example 1

A four necked flask was charged with 345 g of 70% sorbitol and 1147 g of 2-heptylundecanoic acid, to which 1.49 g of sodium hydroxide, 1.15 g of 85% phosphoric acid and 5.69 g of active carbon were added to effect esterification reaction in an nitrogen gas atmosphere at 250° C. for 10 hours. After the reaction, the reaction mixture was filtered to obtain 1205 g of an yellowish oily liquid containing as a major component sorbitan 2-heptylundecanoic acid ester (the average esterification degree: 2.85).

The sorbitan ester thus prepared was reacted with ethylene oxide by bubbling ethylene oxide gas into 100 g of the sorbitan ester in the presence of sodium hydroxide catalyst until 160 moles of ethylene oxide were added per 1 mole of the ester. The reaction mixture was neutralized with phosphoric acid, decolorized with an aqueous hydrogen peroxide solution and filtered to obtain 905 g of pale yellowish solid containing as a major component POE (160) sorbitan 2-heptylundecanoic acid ester (Viscosity Increasing Agent No. 1).

Synthetic Examples 2-7

Viscosity Increasing Agents No. 2-7 listed in the following table were prepared according to the same manner as in Synthetic Example 1.

| Viscosity Increasing Agents | Compounds | Average Degree of Esterification |
|---|---|---|
| No. 2 | POE(120) sorbitan 2-heptyl-undecanoic acid ester | 2.0 |
| No. 3 | POE(200) sorbitan 2-decyl-dodecanoic acid ester | 2.9 |
| No. 4 | POE(160) sorbitan 2-ethyl-hexanoic acid ester | 2.4 |
| No. 5 | POE(150) glycerol 2-heptyl-undecanoic acid ester | 2.0 |
| No. 6 | POE(240) trimethylolpropane 2-heptylundecanoic acid ester | 2.0 |
| No. 7 | POE(250) pentaerythritol 2-heptylundecanoic acid ester | 4.0 |

Synthetic Example 8

Ethylene oxide was bubbled into 91 g of powdery sorbitol in the presence of potassium hydroxide catalyst until 200 moles of ethylene oxide were added per 1 mole of sorbitol, thus obtaining 4450 g of pale yellowish solid containing POE(200) sorbitol ether as a major component.

A four necked flask was charged with 900 g of the thus-obtained sorbitol ether and 115 g of 2-heptylundecanoic acid, to which 1.0 g of sodium hydroxide and 0.77 g of 85% phosphoric acid were added to effect esterification reaction at 245° C. for 20 hours. After the reaction, the mixture was neutralized with phosphoric acid and filtered to obtain 1002 g of pale yellowish solid containing as a major component POE(200) sorbitol 2-heptylundecanoic acid with a degree of esterification of 3.8 (Viscosity Increasing Agent No. 8).

Synthetic Examples 9 and 10

Viscosity Increasing Agents Nos. 9 and 10 below were prepared according to the same manner as in Synthetic Example 8.

| Viscosity Increasing Agents | Compounds | Average Degree of Esterification |
|---|---|---|
| No. 9 | POE(240) glycerol 2-heptyl-undecanoic acid ester | 2.0 |
| No. 10 | POE(300) pentaerythritol 2-decyldodecanoic acid ester | 4.0 |

Synthetic Example 11

Ethylene oxide was bubbled into 140 g of 2-heptylundecanoic acid in the presence of sodium hydroxide catalyst until 200 moles of ethylene oxide were added per 1 mole of the fatty acid, thus obtaining 4412 g of pale yellowish solid containing POE(200) mono-2-heptylundecanoic acid ester as a major component (Viscosity Increasing Agent No. 11).

Synthetic Example 12

A four necked flask was charged with 1000 g of polyethylene glycol having an average molecular weight of 10,000 and 58 g of 2-heptylundecanoic acid, to which 1.02 g of sodium hydroxide was added to effect esterification reaction at 255° C. for 24 hours. The product thus obtained was neutralized with phosphoric acid to obtain 1052 g of pale yellowish solid containing as a major component ethylene glycol di-2-heptylundecanoic acid ester (Viscosity Increasing Agent No. 12).

Experiment 1

Saponification values of viscosity increasing agents prepared in Synthetic Examples 1-12 were measured at different hydrolysis time (1-3 hours) to determine the rates of hydrolysis for theoretical saponification values.

Saponification Value Measurement Method

About 3 g of samples were precisely weighed, to which 20 ml of 0.5N—KOH (alcoholic) was added to effect saponification at 50° C. for 1-3 hours. After saponification, the reaction mixture was reverse-titrated with 0.5N—HCl to obtain the saponification values of the samples and determine rates of hydrolysis for theoretical saponification values. The results are shown in Table 1.

For comparison, saponification values (at saponification time: 1-3 hours) and rates of saponification are given for POE(120) sorbitan dioleic acid ester, POE(120) methylglucoside dioleic acid ester and polyethylene glycol (molecular weight: about 10,000) distearic acid ester.

In the table, "S.V." designates saponification value.

TABLE 1

| Viscosity Increasing Agents | S.V. and Rate of Hydrogenation for Theoretical S.V. (% in parentheses) | | | Theoretical S.V. |
|---|---|---|---|---|
| | 1 Hr | 2 Hrs | 3 Hrs | |
| Inventive Agents | | | | |
| No. 1 | 1.1 (4.8) | 2.7 (9.6) | 3.1 (13.7) | 22.9 |
| No. 2 | 1.7 (4.9) | 3.3 (9.5) | 4.8 (14.0) | 34.6 |
| No. 12 | 0.6 (5.2) | 1.2 (10.3) | 1.7 (14.7) | 11.6 |
| Comparative compounds | | | | |
| POE(120) sorbitan dioleic acid ester | 4.8 (23.2) | 8.6 (41.5) | 11.5 (55.6) | 21.0 |
| POE(120) methylglucoside dioleic acid ester | 4.6 (24.5) | 8.1 (43.1) | 10.8 (57.4) | 18.8 |
| Polyethylene glycol (10,000) distearic acid ester | 3.5 (28.9) | 5.9 (48.8) | 8.0 (66.1) | 12.1 |

EXAMPLE 1

Liquid detergent compositions having the following formulations were prepared according to the conventional method and their viscosities were measured at 25° C. using a B-type viscometer. Results are shown in Table 2.

| | |
|---|---|
| Triethanolamine salt of monolauryl phosphate | 20% by weight |
| Viscosity increasing agent | 0-5% by weight |
| Purified water | balance |
| Total | 100% by weight (pH 7.5) |

TABLE 2

(viscosities are expressed by cps)

| Viscosity Increasing Agents | Concentration of viscosity increasing agent | | | |
|---|---|---|---|---|
| | 0 | 1 wt % | 3 wt % | 5 wt % |
| Inventive Agents | | | | |
| No. 1 | 7 | 9 | 56 | 7460 |

TABLE 2-continued (viscosities are expressed by cps)

| Viscosity Increasing Agents | Concentration of viscosity increasing agent | | | |
|---|---|---|---|---|
| | 0 | 1 wt % | 3 wt % | 5 wt % |
| No. 2 | 7 | 8 | 45 | 1875 |
| No. 3 | 7 | 9 | 52 | 3480 |
| No. 4 | 7 | 8 | 45 | 2600 |
| No. 5 | 7 | 8 | 15 | 1125 |
| No. 6 | 7 | 8 | 40 | 1850 |
| No. 7 | 7 | 8 | 40 | 1700 |
| No. 8 | 7 | 8 | 40 | 1360 |
| No. 9 | 7 | 8 | 25 | 1200 |
| No. 10 | 7 | 8 | 10 | 860 |
| No. 11 | 7 | 8 | 25 | 700 |
| No. 12 | 7 | 8 | 32 | 840 |
| Comparative compound | | | | |
| Polyethylene glycol (10,000) distearic acid ester | 7 | 8 | 30 | 800 |

EXAMPLE 2

Liquid detergent compositions having the following formulations were prepared according to the conventional method and their viscosities were measured at 25° C. using a B-type viscometer. Results are shown in Table 3.

| Triethanolamine salt of monolauryl sulfate | 20% by weight |
|---|---|
| Viscosity increasing agent | 0-5% by weight |
| Purified water | balance |
| Total | 100% by weight (pH 7.5) |

TABLE 3

(viscosities are expressed by cps)

| Viscosity Increasing Agents | Concentration of viscosity increasing agent | | | |
|---|---|---|---|---|
| | 0 | 1 wt % | 3 wt % | 5 wt % |
| Inventive Agents | | | | |
| No. 1 | 6 | 8 | 30 | 300 |
| No. 2 | 6 | 7 | 25 | 260 |
| No. 3 | 6 | 8 | 30 | 280 |
| No. 4 | 6 | 8 | 31 | 350 |
| No. 5 | 6 | 7 | 20 | 280 |
| No. 6 | 6 | 7 | 25 | 300 |
| No. 7 | 6 | 7 | 26 | 320 |
| No. 8 | 6 | 7 | 28 | 250 |
| No. 9 | 6 | 8 | 32 | 360 |
| No. 10 | 6 | 8 | 30 | 320 |
| No. 11 | 6 | 7 | 26 | 265 |
| No. 12 | 6 | 7 | 24 | 240 |
| Comparative compound | | | | |
| Polyethylene glycol (10,000) distearic acid ester | 6 | 8 | 40 | 400 |

EXAMPLE 3

Liquid detergent compositions having the following formulations were prepared according to the conventional method and their viscosities were measured at 25° C. for using a B-type viscometer. Results are shown in Table 4.

| Sodium salt of POE(2.5) lauryl ether sulfate | 20% by weight |
|---|---|
| Viscosity increasing agent | 0-5% by weight |
| Purified water | balance |
| Total | 100% by weight (pH 7.5) |

TABLE 4

(viscosities are expressed by cps)

| Viscosity Increasing Agents | Concentration of viscosity increasing agent | | | |
|---|---|---|---|---|
| | 0 | 1 wt % | 3 wt % | 5 wt % |
| Inventive Agents | | | | |
| No. 1 | 7 | 10 | 90 | 1860 |
| No. 2 | 7 | 8 | 82 | 1500 |
| No. 3 | 7 | 9 | 95 | 2020 |
| No. 4 | 7 | 8 | 60 | 1430 |
| No. 5 | 7 | 8 | 20 | 200 |
| No. 6 | 7 | 8 | 25 | 300 |
| No. 7 | 7 | 8 | 24 | 285 |
| No. 8 | 7 | 8 | 54 | 1260 |
| No. 9 | 7 | 9 | 62 | 1850 |
| No. 10 | 7 | 8 | 30 | 600 |
| No. 11 | 7 | 8 | 22 | 270 |
| No. 12 | 7 | 8 | 25 | 285 |
| Comparative compound | | | | |
| Polyethylene glycol (10,000) distearic acid ester | 7 | 8 | 30 | 350 |

EXAMPLE 4

Liquid detergent compositions having the following formulations were prepared according to the conventional method and their viscosities were measured at 25° C. using a B-type viscometer. Results are shown in Table 5.

| POE(30) lauryl ether | 10% by weight |
|---|---|
| Viscosity increasing agent | 0-5% by weight |
| Purified water | balance |
| Total | 100% by weight (pH 7.5) |

TABLE 5

(viscosities are expressed by cps)

| Viscosity Increasing Agents | Concentration of viscosity increasing agent | | | |
|---|---|---|---|---|
| | 0 | 1 wt % | 3 wt % | 5 wt % |
| Inventive Agents | | | | |
| No. 1 | 6 | 9 | 60 | 2100 |
| No. 2 | 6 | 8 | 45 | 1200 |
| No. 3 | 6 | 9 | 58 | 1850 |
| No. 4 | 6 | 8 | 30 | 860 |
| No. 5 | 6 | 8 | 35 | 1250 |
| No. 6 | 6 | 8 | 35 | 1200 |
| No. 7 | 6 | 8 | 32 | 1000 |
| No. 8 | 6 | 8 | 32 | 1020 |
| No. 9 | 6 | 9 | 40 | 1460 |
| No. 10 | 6 | 9 | 35 | 1220 |
| No. 11 | 6 | 9 | 40 | 950 |
| No. 12 | 6 | 10 | 62 | 2780 |
| Comparative compound | | | | |
| Polyethylene glycol (10,000) distearic acid ester | 6 | 10 | 70 | 3500 |

EXAMPLE 5

Liquid detergent compositions having the following formulations were prepared according to the conventional method, and after having been stored for 0–20 days at 50° C., their viscosities were measured at 25° C. using a B-type viscometer. Results are shown in Table 6.

| Triethanolamine salt of monolauryl phosphate | 20% by weight |
|---|---|
| Viscosity increasing agent | 5% by weight |
| Purified water | 75% by weight |
| Total | 100% by weight (pH 7.5) |

TABLE 6

(viscosities are expressed by cps)

| Viscosity Increasing Agents | Number of Days Stored | | |
|---|---|---|---|
| | 0 | 10 | 20 |
| Inventive Agents | | | |
| No. 1 | 7460 | 7480 | 7520 |
| No. 2 | 1875 | 1780 | 1800 |
| No. 3 | 3480 | 3450 | 3500 |
| No. 4 | 2600 | 2420 | 2580 |
| No. 5 | 1125 | 1100 | 1100 |
| No. 6 | 1850 | 1840 | 1820 |
| No. 7 | 1700 | 1720 | 1650 |
| No. 8 | 1360 | 1385 | 1370 |
| No. 9 | 1650 | 1600 | 1650 |
| No. 10 | 860 | 880 | 860 |
| No. 11 | 700 | 660 | 650 |
| No. 12 | 840 | 820 | 860 |
| Comparative compounds | | | |
| Polyethylene glycol (10,000) distearic acid ester | 800 | 40 | 15 |
| POE(120) methyl-glucoside dioleic acid ester | 1075 | 40 | 18 |

EXAMPLE 6

Liquid detergent compositions were prepared by adding 3% by weight of the viscosity increasing agent to each of an aqueous solution of 15% by weight of triethanolamine salt of monolauryl sulfate (AS/TEA), an aqueous solution of 15% by weight of sodium salt of POE(2.5) laurylether sulfate (ES/Na), and an aqueous solution 15% by weight of triethanolamine salt of monolauryl sulfate plus 1% by weight of NaCl (AS/TEA+NaCl). Transparency of each composition thus prepared are shown in Table 7, in which "TRP" means that the composition is transparent and "TUB" means that the composition is turbid.

The table also shows, for comparison, the transparency of aqueous liquid detergent compositions containing 3% by weight of hydroxyethyl cellulose with molecular weight of about 100,000 (HEC), 3% by weight of methyl cellulose with molecular weight of about 90,000 (MC) and 3% by weight of polyvinyl pyrrolidone of approximate molecular weight of 100,000 (PVP).

TABLE 7

| Viscosity Increasing Agents | Detergent | | |
|---|---|---|---|
| | AS/TEA | ES/Na | AS/TEA + NaCl |
| Inventive Agents | | | |
| No. 1 | TRP | TRP | TRP |
| No. 2 | TRP | TRP | TRP |
| No. 3 | TRP | TRP | TRP |
| No. 4 | TRP | TRP | TRP |
| No. 5 | TRP | TRP | TRP |
| No. 6 | TRP | TRP | TRP |
| No. 7 | TRP | TRP | TRP |
| No. 8 | TRP | TRP | TRP |
| No. 9 | TRP | TRP | TRP |
| No. 10 | TRP | TRP | TRP |
| No. 11 | TRP | TRP | TRP |
| No. 12 | TRP | TRP | TRP |
| Comparative compounds | | | |
| HEC | TRP | TUB | TUB |
| MC | TRP | TUB | TUB |
| PVP | TRP | TUB | TUB |

EXAMPLE 7

Liquid detergent compositions having the following formulations were prepared according to the conventional method and their viscosities were measured at 30° C. using a BM-type viscometer. Results are shown in Table 8.

| 2-alkyl-N—carboxymethyl-N—hydroxyethylimidazolinium betaine* | 10% by weight |
|---|---|
| Viscosity increasing agent No. 4 | 0–3% by weight |
| Purified water | balance |
| Total | 100% by weight (pH 7.0) |

*Milanol C2M CONC (product of Milanol Co.)

TABLE 8

(viscosities are expressed by cps)

| Viscosity Increasing Agents | Concentration of viscosity increasing agent | | | | |
|---|---|---|---|---|---|
| | 0 | 0.5 wt % | 1 wt % | 2 wt % | 3 wt % |
| Inventive Agent | | | | | |
| No. 4 | 6 | 420 | 1836 | 3800 | 4660 |
| Comparative compound | | | | | |
| Polyethylene glycol (10,000) distearic acid ester | 6 | 196 | 1400 | 2520 | 3540 |

EXAMPLE 8

Liquid detergent compositions having the following formulations were prepared according to the conventional method and their viscosities were measured at 30° C. using a BM-type viscometer. Results are shown in Table 9.

| Sodium sulfate of POE(2.5) lauryl ether* | 10% by weight |
|---|---|
| Lauric acid diethanol amide | 0–3% by weight |
| Viscosity increasing agent No. 4 | 0.5% by weight |
| Purified water | balance |
| Total | 100% by weight (pH 7.0) |

*Emal 20C (product of Kao Corp.)

TABLE 9

| Viscosity Increasing Agent | (viscosities are expressed by cps) | | | |
|---|---|---|---|---|
| | Concentration of lauric acid diethanol amide | | | |
| | 0 | 1 wt % | 2 wt % | 3 wt % |
| Inventive Agent No. 4 (0.5 wt %) | 7 | 460 | 1820 | 3640 |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A water soluble viscosity increasing agent, consisting essentially of at least one α-branched fatty acid ester selected from the group consisting of:
   (i) an ester of an adduct of 40 to 400 moles of ethylene oxide with one mole of a polyhydric alcohol and an α-branched fatty acid of 8 to 36 carbon atoms,
   (ii) an ester of polyethylene glycol having an average molecular weight of 2000 to 20,000 and an α-branched fatty acid of 8 to 36 carbon atoms, and
   (iii) an adduct of 40 to 400 mole of ethylene oxide with an ester of a polyhydric alcohol and an α-branched fatty acid of 8 to 36 carbon atoms.

2. The water soluble viscosity increasing agent of claim 1, wherein said α-branched fatty acid has the formula:

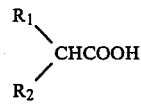

wherein $R_1$ is a linear or branched alkyl or alkenyl group of 4 to 18 carbon atoms and $R_2$ is a linear or branched alkyl or alkenyl group of 2 to 16 carbon atoms.

3. The water soluble viscosity increasing agent of claim 1, wherein said polyhydric alcohol is at least a trivalent alcohol.

4. A liquid detergent composition comprising components (A) and (B) wherein:
   (A) is 5 to 40% by weight of a surface active agent which has detergent action, and
   (B) is 0.1 to 10% by weight of at least one α-branched fatty acid ester selected from the group consisting of:
      (i) an ester of an adduct of 40 to 400 moles of ethylene oxide with one mole of a polyhydric alcohol and an α-branched fatty acid of 8 to 36 carbon atoms,
      (ii) an ester of polyethylene glycol having an average molecular weight of 2,000 to 20,000 and an α-branched fatty acid of 8 to 36 carbon atoms, and
      (iii) an adduct of 40 to 400 mole of ethylene oxide with an ester of a polyhydric alcohol and an α-branched fatty acid of 8 to 36 carbon atoms, said surface active agent (A) component being a member selected from the group consisting of:
         (1) linear or branched alkylbenzenesulfonates having an alkyl group with an average carbon atom content of 10 to 16;
         (2) alkyl- or alkenylether sulfates added to 0.5 to 8 moles, per molecule on the average, of ethylene oxide, propylene oxide, butylene oxide, ethylene oxide/propylene oxide at a ratio of 0.1/9.9 to 9.9/0.1 or ethylene oxide/butylene oxide at a ratio of 0.1/9.9 to 9.9/0.1, said sulfates having an alkyl- or alkenyl group of an average carbon atom content of 10 to 20;
         (3) alkyl- or alkenyl sulfates having an alkyl- or alkenyl group with an average carbon atom content of 10 to 20;
         (4) olefin sulfonates having an average carbon atom content of 10 to 20 per molecule;
         (5) alkane sulfonates having an average carbon atom content of 10 to 20 per molecule;
         (6) salts of a saturated or unsaturated fatty acids having an average carbon atom content of 10 to 24 per molecule;
         (7) alkyl- or alkenylether carboxylates added to, per molecule, 0.5 to 8 moles on the average of ethylene oxide, propylene oxide, butylene oxide, ethylene oxide/propylene oxide at a ratio of 0.1/9.9 to 9.9/0.1 or ethylene oxide/butylene oxide at a ratio of 0.1/9.9 to 9.9./0.1, said carboxylates having an alkyl- or alkenyl group of an average carbon atom content of 10 to 20;
         (8) salts of an α-sulfofatty acid of the formula:

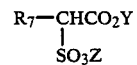

wherein Y is an alkyl group of from 1 to 3 carbon atoms or a counter ion, Z is a counter ion and $R_7$ is an alkyl or alkenyl group of from 10 to 20 carbon atoms, or esters thereof;
         (9) amino acid surface active agents of the formulae:

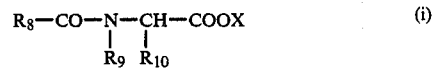

wherein $R_8$ is an alkyl- or alkenyl group of from 8 to 24 carbon atoms, $R_9$ is hydrogen or an alkyl group of 1 or 2 carbon atoms, $R_{10}$ is an amino acid group residue and X is an alkali or alkaline earth metal ion;

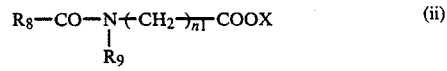

wherein $R_8$, $R_9$ and X have the same meanings as defined above, and n1 is an integer of 1 to 5;

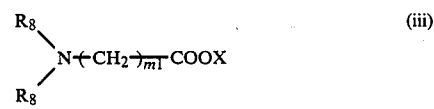

wherein $R_8$ and X have the same meanings as defined above, and m1 is an integer of 1 to 8;

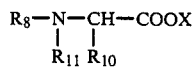  (iv)

wherein $R_8$, $R_{10}$ and X have the same meanings as defined above and $R_{11}$ is hydrogen or an alkyl or hydroxyalkyl group of 1 to 2 carbon atoms;

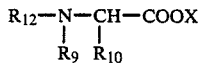  (v)

wherein $R_9$, $R_{10}$ and X have the same meanings as defined above and $R_{12}$ is a β-hydroxyalkyl or β-hydroxyalkenyl group of from 6 to 28 carbon atoms, and

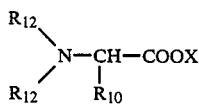  (iii)

wherein $R_{10}$, $R_{12}$ and X have the same meanings as defined above;

(10) phosphoric acid ester surface active agents selected from the group consisting of:
  (i) acidic alkyl- or alkenyl phosphoric acid esters of the formula:

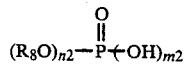

wherein $R_8$ has the same meaning as defined above, and n2 and m2 are values which satisfy the equation, $n2+m2=3$, provided that n2 is a value of 1 or 2;

(ii) alkyl- or alkenyl phosphoric acid esters represented by the formula:

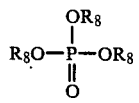

wherein $R_8$ has the meaning as defined above;

(iii) salts of an alkyl- or alkenyl phosphoric acid ester of the formula:

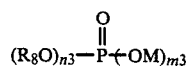

wherein $R_8$ has the same meaning as defined above, M denotes sodium, potassium or calcium, and n3 and m3 are values which satisfy the equation $n3+m3=3$, provided that n3 is a value of 1 to 3;

(11) sulfonic acid amphoteric surface active agents selected from the group consisting of:

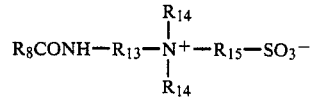  (i)

wherein $R_8$ has the same meaning as defined above, $R_{13}$ is an alkylene group of 1 to 5 carbon atoms, $R_{14}$ is an alkyl group of 1 to 4 carbon atoms, and $R_{15}$ is an alkylene or hydroxyalkylene group of 1 to 4 carbon atoms,

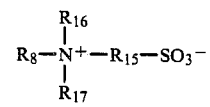  (ii)

wherein $R_8$ and $R_{15}$ have the same meanings as defined above, $R_{16}$ and $R_{17}$ each independently is an alkyl group of 8 to 24 carbon atoms or an alkenyl group of 1 to 5 carbon atoms;

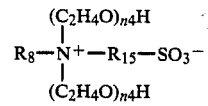  (iii)

wherein $R_8$ and $R_{15}$ have the same meanings as defined above and n4 designates an integer of from 1 to 20;

(12) a betaine amphoteric surface active agent selected from the group consisting of:

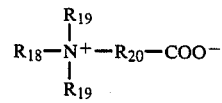  (i)

wherein $R_{18}$ is an alkyl, alkenyl, β-hydroxyalkyl or β-hydroxyalkenyl group of from 8 to 24 carbon atoms $R_{19}$ is a $C_{1-4}$ alkyl group, $R_{20}$ is an alkylene or hydroxyalkylene group of from 1 to 6 carbon atoms;

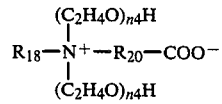  (ii)

wherein $R_{18}$, $R_{20}$ and n4 have the same meanings as defined above; and

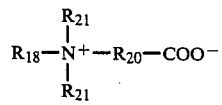  (iii)

wherein $R_{18}$, $R_{20}$ have the same meanings as defined above and $R_{21}$ is a carboxyalkyl or hydroxyalkyl group;

(13) polyoxyethylenealkyl- or alkenyl ethers added to from 1 to 20 moles of ethylene oxide and having an alkyl or alkenylene group of an average carbon atom content of from 10 to 20;

(14) polyoxyethylenealkylphenylethers added to from 1 to 20 moles of ethylene oxide and having an alkyl group of an average carbon atom content of from 6 to 12;

(15) polyoxypropylenealkyl- or alkenyl ethers added to from 1 to 20 moles of propylene oxide and having an alkyl or alkenyl group of an average carbon atom content of from 10 to 20;

(16) polyoxybutylenealkyl- or alkenyl ethers added to from 1 to 20 moles of butylene oxide and having an alkyl or alkenyl group of an average carbon atom content of from 10 to 20;

(17) nonionic surface active agents which are a total of 1 to 30 moles of ethylene oxide/propylene oxide or ethylene oxide/butylene oxide addition compounds, the ratio of ethylene oxide/propylene oxide or ethylene oxide/butylene oxide being 0.1/9.9 to 9.9/0.1, and which have an alkyl or alkenyl group of an average carbon atom content of from 10 to 20;

(18) higher fatty acid alkanol amides of the formula:

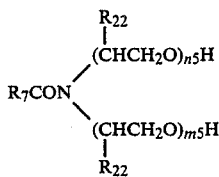

wherein $R_7$ has the same meaning as defined above, $R_{22}$ is hydrogen or methyl, n5 designates an integer of from 1 to 3, and m5 designates an integer of from 0 to 3; or alkylene oxide adducts thereof;

(19) glycerol monoesters of a fatty acid having an average carbon atom content of from 10 to 20;

(20) alkylamine oxides of the formula:

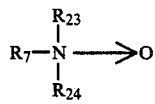

wherein $R_7$ has the same meaning as defined above, $R_{23}$ and $R_{24}$ each independently is an alkylene group of from 1 to 3 carbon atoms; and

(21) cationic surface active agents of the formulae:

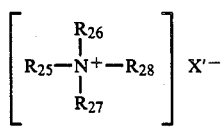  (i)

wherein at least one of $R_{25}$, $R_{26}$, $R_{27}$ and $R_{28}$ is an alkyl- or alkenyl group of from 8 to 24 carbon atoms and the remaining R groups each are an alkyl group of 1 to 5 carbon atoms, and X' is a halogen;

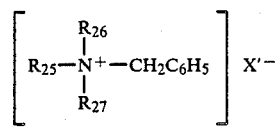  (ii)

wherein $R_{25}$, $R_{26}$, $R_{27}$ and X' have the same meanings as defined above; and

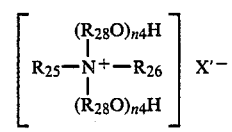  (iii)

wherein $R_{25}$, $R_{26}$, X' and n4 have the same meanings as defined above, and $R_{28}$ is an alkylene group of from 2 to 3 carbon atoms.

5. The water soluble viscosity increasing agent of claim 4, wherein said α-branched fatty acid has the formula:

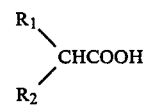

wherein $R_1$ is a linear or branched alkyl or alkenyl group of 4 to 18 carbon atoms and $R_2$ is a linear or branched alkyl or alkenyl group of 2 to 16 carbon atoms.

6. The water soluble viscosity increasing agent of claim 4, wherein said polyhydric alcohol is at least a trivalent alcohol.

7. The liquid detergent composition of claim 4, wherein said α-branched fatty acid is a member selected from the group consisting of 2-ethylhexanoic acid, 2-ethyl-iso-hexanoic acid, 2-propylheptanoic acid, 2-propyl-iso-heptanoic acid, 2-butyloctanoic acid, 2-isobutyloctanoic acid, 2-pentylnonanoic acid, 2-iso-pentylnonanoic acid, 2-hexyldecanoic acid, 2-hexyl-iso-decanoic acid, 2-butyldodecanoic acid, 2-iso-butyldodecanoic acid, 2-heptylundecanoic acid, 2-iso-heptylundecanoic acid, 2-iso-heptyl-iso-undecanoic acid, 2-dodecylhexanoic acid, 2-iso-dodecylhexanoic acid, 2-octyldodecanoic acid, 2-iso-octyldodecanoic acid, 2-octyl-iso-dodecanoic acid, 2-nonyltridecanoic acid, 2-iso-nonyl-iso-tridecanoic acid, 2-decyldodecanoic acid, 2-iso-decyldodecanoic acid, 2-decyl-iso-dodecanoic acid, 2-decyltetradecanoic acid, 2-octylhexadecanoic acid, 2-iso-octylhexadecanoic acid, 2-undecylpentadecanoic acid, 2-iso-undecylpentadecanoic acid, 2-dodecylheptadecanoic acid, 2-iso-dodecyl-iso-heptadecanoic acid, 2-decyloctadecanoic acid, 2-decyl-iso-octadecanoic acid, 2-tridecylheptadecanoic acid, 2-iso-tridecyl-iso-heptadecanoic acid, 2-tetradecyloctadecanoic acid, 2-iso-tetradecyloctadecanoic acid, 2-hexadecylhexadecanoic acid, 2-hexadecyltetradecanoic acid, 2-hexadecyl-iso-hexadecanoic acid, 2-iso-hexadecyl-iso-hexadecanoic acid, 2-pentadecylnonadecanoic acid, 2-iso-pentadecyl-iso-nonadecanoic acid, 2-tetradecylbehenic acid, 2-iso-tetradecylbehenic acid, 2-iso-tetradecyl-iso-behenic acid, 2-tetradecyl-iso-behenic acid, and 2-iso-tetradecyl-iso-behenic acid.

8. The liquid detergent composition of claim 4, wherein said polyhydric alcohol is glycerol, trimethylolpropane, pentaerylthritol, arabinitol, xylitol, sorbitol, mannitol, galactitol, heptytol, inositol, sorbitan, sorbide, glucose, galactose, mannose, maltose, fructose, sucrose, lactose, maltitol, lactitol, methylglucoside, methylgalactoside, methylmannoside, and methylmaltoside.

9. The liquid detergent composition of claim 4, wherein said surface active agent component (A) is a linear or branched alkyl sulfate anionic surface active agent having an average carbon atom content of from 10 to 16, a polyoxyethylene alkyl sulfate constituted of 0.5 to 8 moles of POE added per molecule and having an alkyl group whose average carbon atom content ranges from 8 to 20, an alkyl phosphate having an average carbon atom content of from 8 to 16, an olefin sulfonate having an average carbon atom content of from 10 to 16, a higher fatty acid mono- or dialkanol amide nonionic surface active agent having an average carbon atom content of from 10 to 14, or an amphoteric alkylamine oxide, alkyl betaine or imidazoline surface active agent, each of which has an average carbon atom content of from 10 to 14.

* * * * *